United States Patent [19]

Boebel

[11] Patent Number: 4,503,843
[45] Date of Patent: Mar. 12, 1985

[54] HYSTEROSCOPES

[75] Inventor: Manfred Boebel, Oetisheim, Fed. Rep. of Germany

[73] Assignee: Richard Wolf GmbH, Fed. Rep. of Germany

[21] Appl. No.: 462,003

[22] Filed: Jan. 28, 1983

[30] Foreign Application Priority Data

Jan. 28, 1982 [DE] Fed. Rep. of Germany ....... 3202693

[51] Int. Cl.³ .............................................. A61B 1/00
[52] U.S. Cl. ......................................................... 128/4
[58] Field of Search ........................................ 128/4–8, 128/3

[56] References Cited

U.S. PATENT DOCUMENTS

| | | | |
|---|---|---|---|
| 1,127,948 | 2/1915 | Wappler | 128/7 |
| 1,627,941 | 5/1927 | Wappler | 128/7 |
| 2,487,502 | 11/1949 | Willinsky | 128/4 |
| 3,866,601 | 2/1975 | Russell | 128/4 |
| 3,870,048 | 3/1975 | Yoon | 128/4 |
| 3,882,852 | 5/1975 | Sinnreich | 128/4 |
| 4,085,743 | 4/1978 | Yoon | 128/6 |
| 4,137,920 | 2/1979 | Bonnet | 128/7 |
| 4,254,762 | 3/1981 | Yoon | 128/4 |
| 4,257,420 | 3/1981 | Terayani | 128/4 |
| 4,430,996 | 2/1984 | Bonnet | 128/4 |

Primary Examiner—Edward M. Coven
Assistant Examiner—Max F. Hindenburg
Attorney, Agent, or Firm—Hill, Van Santen, Steadman & Simpson

[57] ABSTRACT

The present invention relates to a hysteroscope which is insertable into the uterus via an entrance adaptor, and consists in a guiding element intended for firm and rigid connection to the entrance adaptor and may be pushed together and pulled apart telescopically by means of handles, a hysteroscope shaft comprising an optical system being insertable through said guiding element and through the entrance adaptor and adapted to be coupled to the proximal extremity of the guiding element.

8 Claims, 6 Drawing Figures

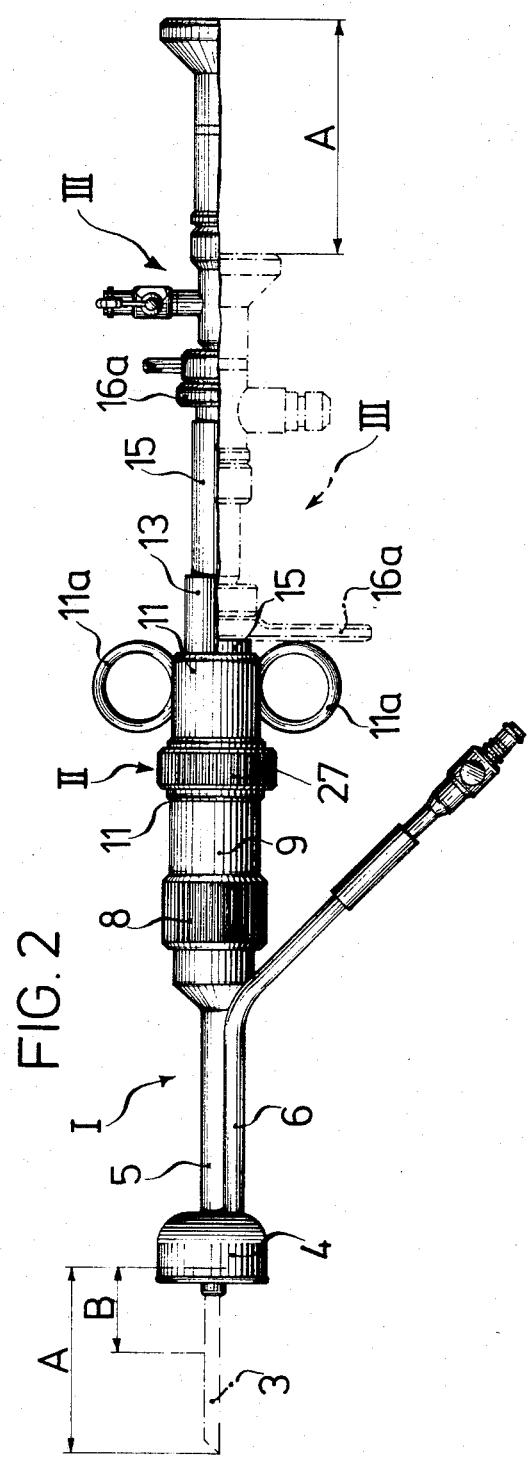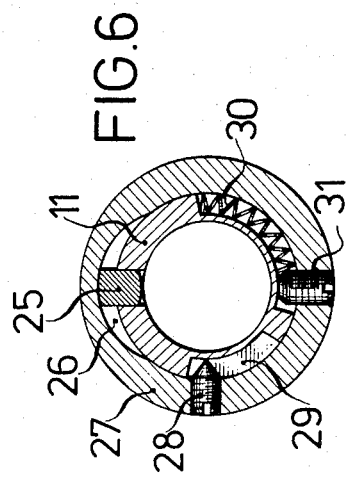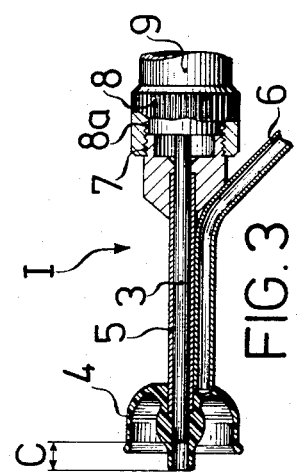

HYSTEROSCOPES

BACKGROUND OF THE INVENTION

The present invention relates to hyteroscopes of the kind having a shaft comprising an optical system which may be passed through an entrance adaptor arranged for sealing a patient's uterus by negative pressure and which is insertable into the uterus through the cervical passage. Hereinafter such hysteroscopes will be referred to as "of the kind described".

For complete visual examination of the uterus, it is known e.g. from German Gebrauchsmuster No. 70 36 446 and German Offenlegungschrift No. 2 902 829, to make use of a hysteroscope which is inserted through the cervical passage, the entrance being sealed off by means of a spring-loaded cone. Since this seal proved to be unsatisfactory, a method was adopted in which said seal is replaced by an entrance adaptor which, after being placed over the entrance, is held fast by application of a negative pressure. The hysteroscope shaft having the optical system is inserted into the uterus through a proximal rubber seal of the adaptor. To this end, it is necessary for the physician to hold the adaptor with one hand and the hysteroscope shaft coupled to the optical system with the other hand, which leads to a very unstable arrangement, so that the push and pull displacements of the hysteroscope shaft can no longer be performed quietly and sensitively without risk of injuring the cervical passage and the womb.

Consequently, it is an object of the invention to provide means of assuring that the hysteroscope may be guided calmly and sensitively forward and back through the cervical passage, into and out of the womb.

SUMMARY OF THE INVENTION

In the case of a hysteroscope of the kind described, this problem is resolved in accordance with the invention in that a rigid guiding element is provided, which is screwable to the adaptor at the distal side via a head and is coupled at the proximal side to the hysteroscope shaft, which may be axially pushed together telescopically in the direction towards the screw head or cap nut against a spring system by means of handles and may be turned with the parts comprising the handles with respect to the distal-side cap nut, the length of the guiding element in the idle position being selected or adjustable in such manner that when the entrance adaptor is installed, the distal extremity of the hysterscope shaft is situated at a short distance in front of the opening of the adaptor passage.

The adaptor, the guiding element and the hysterscope shaft comprising an optical system are firmly interconnected thereby and these parts form a firm rigid unit. A smooth and precise movement of the hysteroscope shaft comprising an optical system is assured by the telescopic contraction and automatic extension of the telescopic elements of the guiding member. The unit may thus be operated with one hand only, so that the physician's other hand is available for other actions.

Advantageously moreover to the distal extremity of the hysteroscope shaft may, by telescopic pushing together of the guiding element, be carried from an idle position before the opening of the adaptor into an immobile but releasable position in which the hysteroscope shaft comprising an optical system projects distally out of the adaptor and may be inserted into the cervical passage. Precise centering of the adaptor on the entrance is possible thereby, and after retraction of the extremity of the hysteroscope shaft projecting out of the adaptor it is possible to check on correct seating of the entrance adaptor on the entrance, simply by retracting the optical system into the entrance adaptor so far that the outlet opening of the lead-in within the entrance adaptor appears as a circular delimitation and thereupon by checking on the position of the cervical passage in this delimitation, said passage being due to be situated at the centre of the delimitation if a correct seat prevails.

If a perfect seat of the entrance adaptor is observed, the hysteroscope shaft may then be inserted into the womb via the cervical passage and the womb may be examined visually by means of the optical endoscope system present within the hysteroscope shaft, in which connection it is also possible to make an omnilateral inspection by turning the parts of the guiding element provided with the handles.

After examination, it is merely necessary to turn off the negative pressure applied in the end-side annular chamber of the adaptor and to remove the entrance adaptor from the entrance.

BRIED DESCRIPTION OF THE DRAWINGS

In order that the invention may be more clearly understood, reference will now be made to the accompanying drawings which illustrate one embodiment thereof by way of example and in which:

FIG. 1 is a an axial cross-sectional view through the inventive guiding element, FIG. 2 in a side view the combination of the guiding element according to FIG. 1 with the entrance adaptor screwed thereto and the hysteroscope shaft comprising an optical system with the top half in the idle position and with the bottom half after contraction of the guiding element, FIG. 3 is an axial cross-sectional view through the entrance adaptor screwed to the guiding element with the distal extremity of the hysterscope shaft in the idle position, FIG. 4 is a side a view of the first telescopic tube of guiding element, FIG. 5 is a side view with portions broken away of a tube connected to the first telescopic tube and of a part of a second telescopic tube, and FIG. 6 is a cross-sectional view taken along the line VI—VI of FIG. 1.

DETAILED DESCRIPTION OF THE PREFERRED EMBODIMENT

Figure 1:
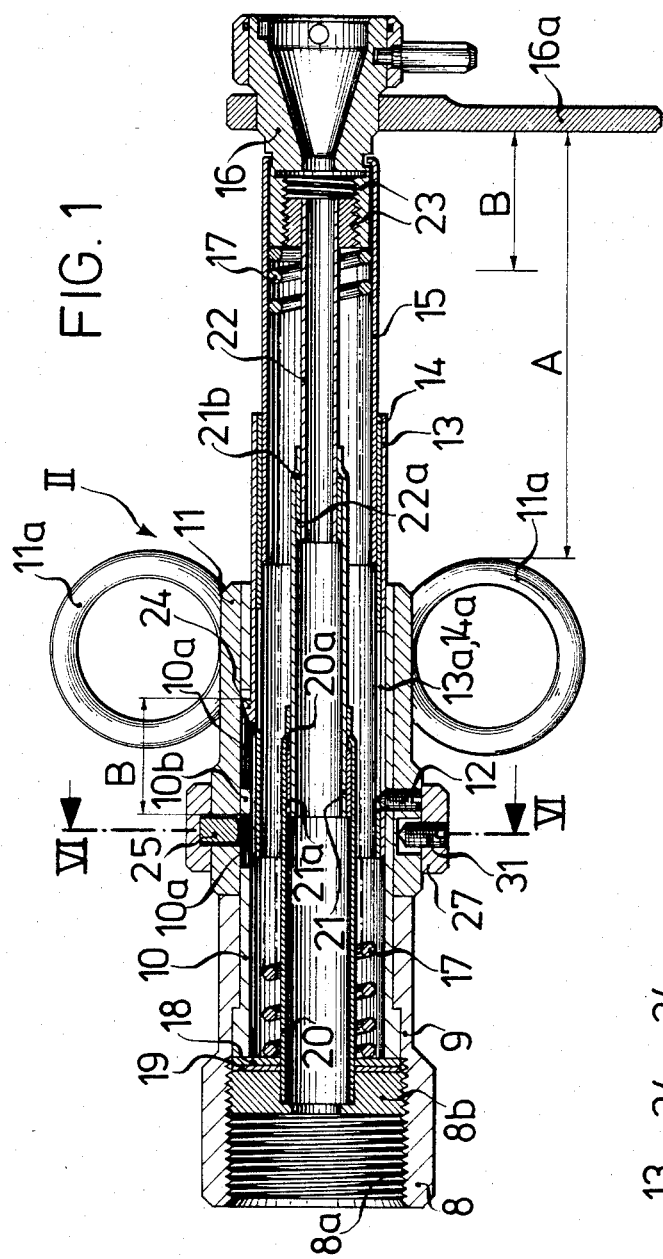

Referring now to the drawings according to the invention, the hysterscope comprises an entrance adaptor I (FIG. 2), a guiding element II (FIGS. 1 and 2) and the hysterscope shaft III comprising an optical system.

The entrance adaptor I comprises an adaptor element 4 which is capable of shutting off the entrance in a sealed manner. The element 4 is connected to a pipe 5 and has a pipe 6 which may be connected to a negative pressure. The pipe 5 is provided with an external screw-thread 7 at the proximal end.

The adaptor I (FIGS. 2 and 3) comprising the proximal outer screw-thread 7 may be screwed into a screw head of cap nut 8 comprising an internal screw-thread 8a and an annular base 8b of the guiding element II (FIGS. 1 and 2). The cap nut 8 is continued by a tubular element 9 in which a first guide tube 10 is fitted in a twistable manner but secured against axial displacement by means of a stop. On a proximal extension of the first guide tube 10, a cylindrical ring 11 comprising two finger grips 11a is firmly joined to the guide guide tube 10 by means of one or more set screws 12. Within the guide tube 10 is axially displaceable a first telescopic tube 13 in which an inner tube 14 is firmly connected. The axial displacement in a direction being limited in that a set screw 12 engages in a longitudinal recess 13a of the first telescopic tube 13. A second telescopic tube 15 is displaceable within the first telescopic tube 13, 14. The second telescopic tube 15 is firmly joined at the proximal side by means of a bayonet joint (not shown) to a known coupling member 16 which carries the second grip or handle 16a and to which may be coupled the proximal portion of a hysteroscope shaft III comprising an optical system. The shaft which passes through the guiding element II and the entrance adaptor I and, in the idle position, terminates with the spacing C (FIG. 3) in front of the opening of the adaptor passage.

A compression spring 17 bearing distally against a steel ring 18 and via an anti-friction ring 19 on the screw-threaded ring 8b screwed distally into the cap nut 8, and proximally against the coupling element 16, extends within the first guide tube 10, the first and second telescopic tubes 13, 14 and 15. The space of the compression spring 17 is internally delimited by a second guide tube 20 firmly joined to the screw-threaded ring 8b, a third telescopic tube 21 axially displaceable therein and within which is displaceable a fourth telescopic tube 22 which is connected to the coupling element 16 by means of a screw-thread 23. The coupling element 16 is displaceable with respect to the proximal extremity of the fourth telescopic tube 22, in such a manner to allow the spacing C (FIG. 3) of the extremity of the distal hysterscope shaft 3 from the opening of the adaptor passage to be adjusted.

Figure 5:
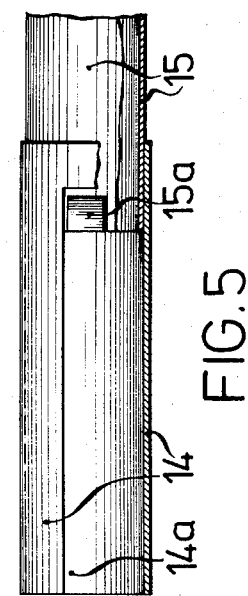
Figure 4:
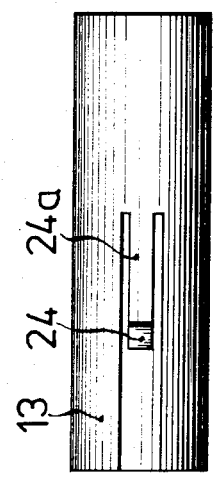

To prevent separation during extension of the guide tubes and of the telescopic tubes, the second guide tube 20 engages proximally with a constriction 20a behind an outer distal ring 21a of third telescopic tube 21, and the third telescopic tube engages with a constriction 21b behind a distally larger stop ring 22a of the fourth telescopic tube 22. Furthermore, the first guide tube 10 is provided in the area of the cylindrical ring 11 with a longitudinal groove 10a which is overbridged at 10b before the distal end. A hooked projection 24 of a springy tongue 24a produced by means of excisions from the telescopic tube 13, 14 presses into the longitudinal groove 10a. The second telescopic tube 15 (FIG. 5) contains another stop 15a which runs in an excision 14a of the telescopic tube section 14 and entrains the telescopic tube 15 in the proximal direction upon extending the telescopic tubes.

A rigid unit is formed after screwing the guiding element II to the entrance adaptor I, and the hysteroscope shaft III comprising an optical system is led through this unit and is coupled to the proximal portion 16, the distal extremity of the shaft 3 terminating with the spacing C in front of the opening of the adaptor passage (FIG. 3). This should be described as the idle position.

If the adaptor I is then to be placed centrally on the entrance, the coupling member 16, together with the hysteroscope shaft 3 and the optical system, is pushed forward by the distance A (FIG. 1) with respect to the cap nut 8 by grasping the annular grips 11a and the handle 16a. This causes telescopic tubes 13, 14 and 15 and the telescopic tubes 21 and 22 to be displaced one into another and in a distal direction in the two guide tubes 10 and 20. The thrust on the grips is then stopped and the telescopic and guide tubes are pushed apart by the action of the compression spring 17 until the hooked projection 24 within the longitudinal recess 10a engages behind the overbridgement 10b and the position reached is retained. Thus the guiding element II is elongated by the compression spring 17 by the distance A minus B, so that the distal extremity of the hysteroscope shaft 3 projects out of the opening of the adaptor I by the distance B minus C (FIG. 2).

The hysteroscope III is inserted in this position, the distal end of the hysteroscope shaft 3 penetrating into the cervical passage whilst doing so until the part 4 of the adaptor I is placed against the entrance and then bears sealingly against the entrance by application of negative pressure. This negative pressure causes the adaptor I to be held fast thereon. A precisely central contact of the entrance adaptor I is thereby obtained. This may be verified by complementarily extending the guiding element II again by the distance B as illustrated in FIG. 2, so that the position of the cervical passage may be observed as already stated in the foregoing. Extending the guiding element II by the distance B is rendered possible by cancelling the engagement of the hooked projection 24 behind the overbridgement 10b. This is accomplished by the fact that the cylindrical ring 11 is provided with a radial bore with a release pin 25. An outer end of the pin 25 (FIG. 6) is situated in an internal cresent-shaped recess 26 of an external operating ring 27 which is twistable to a limited degree. The pin 25 is displaced inwards radially upon turning the ring 27 and pushes the hooked projection 24 of the springy tongue 24a out of the area of the bridge 10b, thereby releasing the telescopic tube 13, 14 which is displaced in the proximal direction by the distance B by means of the spring 17.

The limited twisting displacement of the operating ring 27 may be obtained by the fact that a grub screw 28 of the ring 27 engages in a peripheral groove 29 of the cylindrical ring 11. The return rotation of the ring 27 is performed automatically by means of a spring system 30 which at one end bears against a groove extremity of the cylindrical ring 11 and at the other end against a set screw 31 of the ring 27.

After verifying the precisely central seating of the entrance adaptor I with respect to the cervical passage, the guiding element II may be pushed together again telescopically by actuation of the grips, the distal extremity of the hysteroscope shaft 3 then being insertable into the womb through the cervical passage under observation by means of the optical system.

The handling action may thus by virtue of the rigid overall unit be performed with one hand only, said unit being insertable into the womb centrally, calmly and precisely, through the cervical passage, all the telescopic elements of the guiding element II connected to the annular grips 11a and the handle portion 16a also being twistable around the longitudinal axis of the guiding element with respect to the cap nut 8 to allow of omnilateral inspection of the womb.

I claim:

1. In a hysteroscope having an entrance adaptor being sealably attached to an entrance of a uterus by a negative pressure and having a passage to slidable receive a shaft having an optical system, said shaft being movable through the passage for insertion into the uterus through the cervical passage, the improvements comprising a guiding element having a distal end provided with means for securing the element to the adaptor and a proximal end having means for mounting the shaft with the shaft extending through the element and into the adaptor, said guide element comprising at least a first tube telescopical receiving a second tube, said tubes being movable from an elongated idle position with a majority of the second tube extending out of the first tube to a contracted position with a majority of the second tube being telescopically received in the first tube, handle means for moving the tubes to the contracted position, and spring means for biasing the tubes toward the idle position, the length of the guide element for the idle position being selected so that the distal end of the shaft is positioned adjacent an opening of the passage of the adaptor.

2. In a hysteroscope according to claim 1, wherein the guide element includes means for holding the tubes in an intermediate position with the distal end of the shaft extending a short distance out of the passage to aid in centering the adaptor on the entrance of the uterus.

3. In a hysteroscope according to claim 1, wherein the means for securing includes a sleeve having a cap nut portion with threads for securing the sleeve to the adaptor, said sleeve telescopically receiving the first tube, said guide element including spring guide means comprising at least two guide tubes telescopically connected together and extending from a member of the mounting means to the cap nut portion inside of the sleeve and first and second tubes, said spring means being disposed about the guide means and extending between the member and the cap nut portion, said handle means including finger grips secured to the sleeve and a second handle secured to said member.

4. In a hysteroscope according to claim 3, wherein the first tube has integral spring finger engageable in a slot in the sleeve to limit movement of the first tube in the sleeve, said slot having a stop bridge extending thereacross engaged by the finger to hold the first tube in an intermediate position and means mounted on the sleeve for disengaging the spring finger from the stop bridge.

5. In a hysteroscope according to claim 4, wherein the means for disengaging includes an actuation ring mounted for rotation on the sleeve and having a crescent shaped recess, a movable pin mounted in a hole in the sleeve adjacent the stop bridge, said pin having an end in the recess and the opposite end engageable with the spring finger, and spring means for urging the ring to a position with the pin withdrawn from engagement with said finger.

6. In a hysteroscope according to claim 3, wherein the cap nut portion has an anti-friction ring interposed between a steel ring insert, said steel ring insert being engaged by the spring means.

7. In a hysteroscope according to claim 4, wherein the second tube has stop means received in a slot of the first tube to limit the amount of movement of the second tube in the direction of the idle position.

8. In a hysteroscope according to claim 3, wherein the guide means is connected to the member of the mounting means by an adjustable threaded connection so that the effective length of the guide element can be obtained by said threaded connection.

* * * * *